United States Patent [19]

Freenor, III et al.

[11] 4,289,909
[45] Sep. 15, 1981

[54] PROCESS FOR PREPARING 1-DICHLOROACYL-4-SUBSTITUTED PHENOXY BENZENE AND INTERMEDIATES THEREFOR

[75] Inventors: Francis J. Freenor, III, Richmond; Barbara M. Koerber, Berkeley, both of Calif.

[73] Assignee: Chevron Research, San Francisco, Calif.

[21] Appl. No.: 126,252

[22] Filed: Mar. 3, 1980

[51] Int. Cl.$^3$ ............... C07C 45/46; C07C 45/63; C07C 41/91
[52] U.S. Cl. ........................... 568/315; 568/322; 568/635
[58] Field of Search ............ 568/635, 322, 323, 331, 568/316, 315

[56] References Cited

U.S. PATENT DOCUMENTS

| | | | |
|---|---|---|---|
| 2,004,069 | 6/1935 | Bruson et al. | 568/323 |
| 2,095,619 | 10/1937 | Stoesser et al. | 568/635 |
| 2,390,368 | 12/1945 | Hochwalt | 568/323 |
| 3,487,114 | 12/1969 | Irick et al. | 568/635 |
| 3,966,826 | 6/1976 | Traken | 568/637 |
| 4,031,131 | 6/1977 | Johnson | 560/21 |

FOREIGN PATENT DOCUMENTS 7806111  12/1978  Netherlands ............ 568/635

OTHER PUBLICATIONS

Kirt-Otheim, Encyclopedia of Chemical Tech., vol. 10, pp. 147-150.
Aston et al., Org. Synth. Cal., vol. #3, pp. 538-541 (1955).

*Primary Examiner*—Natalie Trousof
*Assistant Examiner*—James H. Reamer
*Attorney, Agent, or Firm*—D. A. Newell; T. G. DeJonghe; L. S. Squires

[57] ABSTRACT

Processes for preparing 1-dichloroacyl-4-(substituted phenoxy)benzenes and intermediates therefor. The processes are characterized by the use of certain catalysts, solvents and reaction conditions which afford improved yields and reaction products which can be purified by simple procedures (e.g. extraction, crystallization, etc.). The processes are especially applicable to manufacturing large quantities of the aforementioned compounds. The products are useful as mite ovacides.

14 Claims, No Drawings

PROCESS FOR PREPARING 1-DICHLOROACYL-4-SUBSTITUTED PHENOXY BENZENE AND INTERMEDIATES THEREFOR

BACKGROUND OF THE INVENTION

1. Field of the Invention

This invention relates to processes for preparing 1-dichloroalkanoyl-4-(substituted phenoxy)benzenes and to processes for preparing certain intermediates therefor.

2. The Prior Art

U.S. Pat. No. 3,966,826 discloses the preparation of 1-hydroxy-4-(2-chloro-4-trifluoromethylphenoxy)benzene via the reaction of the potassium salt of hydroquinone with 3,4-dichlorobenzotrifluoride (i.e., 1,2-dichloro-4-trifluoromethylbenzene) followed by acid hydrolysis. Patentee also teaches that the addition reaction is conducted at 120° to 200° C. in the presence or absence of a copper catalyst. U.S. Pat. No. 4,031,131 discloses the preparation of 1-carboxy-3-(2-chloro-4-trifluoromethylphenoxy)benzene and esters thereof by reacting a disalt of 3-hydroxybenzoic acid with 1,2-dichloro-4-trifluoromethylbenzene in a polar aprotic organic solvent such as dimethylsulfoxide, dimethylformamide, sulfolane, N-methyl-2-pyrrolidone, hexamethylphosphoric triamide, etc. Chemical Abstracts discloses that Japanese Pat. No. 75:58,228 discloses the preparation of 1-acetyl-4-(2-chloro-4-trifluoromethylphenoxy)benzene.

It is also known that diaryl ethers can be synthesized by an Ullmann coupling of aryl halides with metal phenolates; e.g. see The Merck Index—Ninth Edition, p. ONR-89, Merck & Co., Inc. (1976). The preparation of dichloroacetophenone via the chlorination of acetophenone in glacial acetic acid is described in Organic Synthesis Vol. 3, p. 538 (1955).

U.S. patent application Ser. No. 126,254, filed on even date herewith by John W. Kobzina, discloses certain novel 1-dichloroalkanoyl(substituted phenoxy)benzenes, which are useful as mite ovacides, which disclosure is hereby incorporated by reference. Such compounds include 1-dichloroacetyl-4-(2-chloro-4-trifluoromethylphenoxy)benzene and 1-dichloroacetyl-4-(2-trifluoromethyl-4-chlorophenoxy)benzene.

One of the problems associated with the preparation of these compounds is the separation of the compounds from isomers and other unidentified impurities formed in the reaction product. Such impurities are formed during the preparation of the product and also during the preparation of the intermediates therefor. The separation of such impurities from the products and intermediates is very difficult on a large scale basis because, among other problems, of the solubility of both the products, intermediates and impurities in commercial solvents, such as hexane, etc. Thus, while the products and intermediates can be separated by sophisticated laboratory techniques, such as high pressure liquid chromatography, such techniques are not commercially practical for large scale production.

SUMMARY OF THE INVENTION

The present invention provides processes for preparing 1-dichloroalkanoyl-4-(substituted)benzenes and intermediates therefor, in improved yields and purities, which can be readily purified without resort to sophisticated laboratory techniques. This improvement cannot be attributable to any one isolated reaction condition but rather depends upon the use of a particular combination of reaction conditions, catalyst, solvents and reaction sequence, in accordance with the present invention.

In one embodiment the invention provides an improved process for preparing 4-(chloro-trifluorophenoxy)benzene chlorides via the reaction of an alkali metal phenolate with a substituted benzene chloride in the presence of a copper catalyst in dimethylsulfoxide (solvent) at high concentrations under carefully controlled temperature conditions.

In a further embodiment the invention provides an improved process for preparing 1-alkanoyl-4-(chloro-trifluoromethylphenoxy)benzene via the reaction of the appropriate 4-(substituted phenoxy)benzene with acetyl chloride in the presence of ferric chloride (Friedel Crafts catalyst) in methylene chloride using about equal molar quantities of the reactants and ferric chloride and conducting the reaction under carefully controlled temperature conditions.

In another embodiment the invention provides an improved process for preparing 1-dichloroalkanoyl-4-(substituted phenoxy)benzenes which comprises one, or preferably both, of the aforedescribed processes and the step of reacting a 1-alkanoyl-4-(substituted phenoxy)benzene with chlorine at temperatures in the range of about from 25° to 65° C.

The invention will be further described hereinbelow.

FURTHER DESCRIPTION OF THE INVENTION AND PREFERRED EMBODIMENTS

The processes of the invention can be respectively schematically represented by the following overall reaction equations:

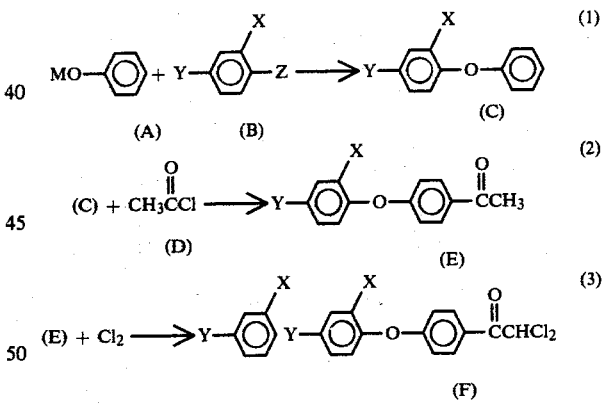

wherein M is an alkali metal; one of X or Y is chloro and the other is trifluoromethyl; Z is fluoro, chloro or bromo, preferably chloro.

The process (1) of the invention for preparing the compounds of formula C can be conducted by contacting the substituted benzene halide (B) with an alkali metal phenolate (A) in dimethyl sulfoxide (solvent) in the presence of a copper catalyst at temperatures in the range of about from 145° to 165° C. preferably about from 150°–160° C., under substantially anhydrous conditions.

This process affords very high yields (for example, above 90% based on compound B) of intermediate C and affords a reaction product mixture which is sufficiently free of isomers or other impurities that, upon removal of the solvent, the intermediate C can be directly used in the next process step of the invention.

The improvement afforded by this process is the result of using a particular combination of reaction temperature, solvent and catalyst. Thus, it is necessary to conduct the reaction at the temperatures specified above using dimethyl sulfoxide as the solvent and a copper catalyst (preferably powdered copper, though other copper catalysts, e.g., copper halides, etc. can also be used). If any one of these conditions are not met, much poorer results are obtained in terms of product (C) purity and yields. The reaction will also take place in dimethylsulfoxide without the copper catalyst, however, we have found that the copper catalyst affords a multifold increase in reaction rates and a corresponding reduction in reaction time.

If the temperature is maintained below the prescribed range, the reaction will proceed at a very slow, or insignificant, rate and if the reaction temperature exceeds the prescribed range, the reaction rate increases too much, dramatically increasing the formation of impurities which are difficult to remove. The reaction is exothermic and takes place rapidly upon contact of the reactants. We have found that it is important to control the rate of addition of the reactants to each other such that the temperature of the reaction mixture does not exceed the temperature range prescribed above. We have also found that it is preferred to add reactant B to a mixture of reactant A, catalyst and solvent.

Typically, reaction times in the range of the time of addition of the second reactant to the reaction mixture plus about from ¼ to 24 hours are used.

Generally, a mol ratio in the range of about from 1 to 1.1 mol, preferably about 1 to 1.03 mol of reactant A is used per mol of reactant B. Generally, only a small amount of copper catalyst, commonly referred to as a catalytically effective amount, is used. In more finite terms, typically a catalyst ratio in the range of about from 0.5 to 5 grams of copper catalyst, based on copper content, and preferably about 1.5 to 2.5 grams of copper catalyst, per g-mol of reactant A is used.

Preferably high reactant concentrations are used and thus preferably, the least amount of dimethylsulfoxide that will afford a workable liquid mixture of the reactants is used. We have found that the high reactant concentration affords improved (faster) reaction rates which do not adversely affect product purity so long as the prescribed temperature control is maintained. Typically, about from 2 to 6 mol, preferably about 3–5 mol of reactant B is used per liter of dimethylsulfoxide.

The product C is sufficiently pure that it can be used directly in process (2) of the invention, after removal of the solvent. If desired, the product C could also be further purified by relatively simple procedures such as, for example, extraction, crystallization, evaporation, distillation, etc., which lend themselves to large scale commercial use.

Suitable compounds of formula A which can be used include, for example, sodium phenolate; potassium phenolate and the like. Suitable compounds of formula B which can be used include, for example, 1,2-dichloro-4-trifluoromethylbenzene; 1,4-dichloro-2-trifluoromethylbenzene; 1-bromo-2-chloro-4-trifluoromethylbenzene; 1-fluoro-2-trifluoromethyl-4-chlorobenzene and the like. Generally, best results are obtained by using the compound of formula B wherein Z is chloro.

The starting materials of formulas A and B are known materials and can be obtained from known sources or known procedures.

The present process can also be conveniently carried out in situ with the preparation of the alkali metal phenolate, via the reaction of an alkali metal hydroxide with phenol, after removal of the water byproduct and co-solvent, as illustrated in Example 1 hereinbelow. We have also found that best results are obtained by preparing the alkali metal phenolate using dimethylsulfoxide and toluene as co-solvents. Also, high purity reactants should be used to minimize impurities.

The second process (2) of the invention may be categorized as a Friedel Crafts reaction.

The prior art has generally conducted Friedel Crafts reaction using about 2 mols of Friedel Crafts catalyst per mol of acetyl chloride (D) and has used a variety of Friedel Crafts catalysts and solvents. We have discovered that the catalyst, solvent, catalyst ratio and sequence of addition of the reactants are all critical to obtaining the improved product purity afforded by the present invention. Thus, we have found that ferric chloride must be used as the catalyst and methylene chloride must be used as the solvent. If other Friedel Crafts catalyst (e.g. boron fluoride) or other solvents (e.g., carbon disulfide, hexane, etc.) are used, much poorer reaction rates and/or large amounts of isomer impurities are obtained. Also, certain Friedel Crafts catalysts, such as the conventional Friedel Crafts catalyst aluminum chloride, cannot be used because they attack the trifluoromethyl substituent. We have further found that conducting this reaction using a catalyst ratio of about 2 mols of Friedel Crafts catalyst per mol of acetyl chloride (D), affords a product (E) having a large amount of undesired isomer impurities which require sophisticated separation procedure. We have now unexpectedly discovered that by reducing the catalyst ratio to about from 1 to 1.3 mols, and preferably about from 1 to 1.15 mols, of ferric chloride per mol of acetyl chloride (D) that impurities, which are difficult to separate are very sufficiently reduced without a commercially significant sacrifice in reaction rate.

We have further found that the sequence of contacting the reactants is also important, thus we have found that by adding reactant C at a controlled rate to a mixture of acetyl chloride (D), solvent and catalyst that the reaction can be conducted at higher temperatures and correspondingly higher reaction rates than if acetyl chloride is added to a mixture of reactant C, solvent and catalyst. If the latter method is attempted, substantial quantities of difficult-to-separate impurities are produced.

Thus, it is stressed that the present invention requires all four conditions (i.e., solvent, catalyst catalyst ratio and order of reactant addition) must be met. If all four conditions are not met, the reaction either does not occur or proceed at such a slow rate as to be unacceptable, and/or produces substantial quantities of impurities which are difficult to remove. The reaction product of the present process still contains impurities but these impurities can be removed by simple procedures such as extraction, derivatization-hydrolysis, crystallization, precipitation and the like.

We have also found that temperature control is very important because at higher temperatures, the amount of isomeric impurities substantially increases. Thus, we have found that this reaction should be conducted at temperatures in the range of about from 0° to 30° C. and preferably about from 15° to 25° C. Also, because the reaction is highly exothermic, temperature control is not an easy matter. Thus, even conducting the reaction at room temperature, requires the use of external cooling means to prevent the reaction mixture from exceeding the prescribed temperature. Further, since the reaction rate increases with temperature, the problem compounds itself. One advantageous method of handling this problem is to add reactant C to reactant D at a controlled rate such that they are substantially consumed (react) as they are contacted with each other, thereby resulting in a substantially uniform rate of heat generation which can be dissipated by conventional heat exchange means. If the temperature of the reaction mixture is too high, then, of course, the problems already discussed above, occur. However, the temperature of the reaction mixture can also not be too low, because then the reactants will not react fast enough. This will result in a build-up of reactants which will ultimately react generating unprovided for heat which will overload the cooling system ultimately causing the temperature of the reaction mixture to rise undesirably.

Typically, about from 1 to 1.5 mols and preferably about 1 to 1.2 mols of compound D are used per mol of compound C. As with the first process embodiment, it is preferred to use the least amount of methylene chloride (solvent) which will afford a workable liquid mixture of reactants C and D. Typically, a solvent concentration in the range of about from 1 to 10 mols, and preferably about from 2 to 5 mols of reactant C per liter of methylene chloride is used. Typically, reaction times in the range of the addition time of the reactants to each other plus about from ½ to 24 hours are used. Also, the reaction should be conducted under substantially anhydrous conditions.

The use of acetyl chloride as reactant D is also a factor which warrants discussion. Since we have found, that, although this reaction can be conducted using acetic anhydride, that acetic anhydride is difficult to work with because it forms a gum-like mass with the reaction mixture and yields a reaction product having a large amount of difficult-to-separate impurities.

The process of the invention for preparing the mite ovacide products F comprises the chlorination of intermediate E plus process step (2) or preferably both process embodiments (2) and (1), the invention described hereinabove. In conducting this process, the reaction sequence as well as the specific reaction conditions used is important. For example, in theory, the sequence of process steps, could be reversed, that is, in theory, phenol could be acetylated and then converted to the ether. Thus, intermediate E would be prepared by reacting sodium 4-acetylphenone with 1,2-dichloro-4-trifluoromethylphenyl. We have found that, when this reaction is attempted, undesired byproducts, (e.g. the symmetrical phenoxy ether, tars, etc.) are produced in substantial amounts along with the desired intermediate E. Thus, the sequence of the reaction process is also an important factor.

Step (3) in the process of the invention for preparing the product compounds of formula F, can be conducted by contacting the appropriate compound of formula E with chlorine in a suitable inert organic solvent under reactive conditions, and preferably under anhydrous conditions. Again temperature control is important because of the exothermic character of the reaction and the sensitivity of reaction rate and impurity formation to temperature. Thus, the reaction should be conducted at temperatures below about 65° C. to reduce isomer formation and above 15° C. to ensure an acceptable reaction rate. Preferably, the reaction is conducted at temperatures in the range of about from 40°–55° C.

Suitable inert organic solvents which can be used include, for example, glacial acetic acid, carbon tetrachloride, chloroform and the like and compatible mixtures thereof. Best results are obtained using glacial acetic acid. Again, the minimum amount of solvent which renders a workable liquid mixture of reactant E is preferred. Generally, a reactant concentration in the range of about from 1 to 5 mols, preferably about from 2 to 4 mols of compound E per liter of solvent are used. Best results are obtained using glacial acetic acid.

Typically about from 2 to 2.5, and preferably about from 2.1 to 2.3 mols of chlorine ($Cl_2$) are added per mol of compound of formula E. Typically, reaction time in the range of the chlorine addition time plus about from ¼ to 24 hours are used.

By following the procedures of the present invention, the product of formula F can be recovered from the reaction product in purities of 90% or higher by simple procedures such as, for example, extraction, precipitation, crystallization, evaporation and the like.

Thus, the present invention provides an improved process readily applied to the commercial large scale manufacture of the mite ovacides of formula F. These processes can be conducted as batch processes, continuous processes or semi-continuous processes.

Illustrative examples of specific purification procedures for each of the above described processes are set forth in the respective Examples set forth hereinbelow. However, it should be appreciated that other suitable procedures could also be used.

UTILITY

The compounds of formula F are described by John W. Kobzina in U.S. Ser. No. 126,254, filed on even date herewith, as exhibiting substantial mite ovacide activity and useful for killing mite eggs. As described in the aforementioned patent application, the compounds can be applied, in an effective mite ovacidal amount, to mite eggs, or surfaces subject to mite eggs, via any suitable procedures. Importantly, the present compounds do not exhibit any significant herbicidal activity and thus can be safely applied to vegetation to control mites via the destruction of their eggs.

These compounds can be stored and applied as formulations incorporated with compatible biologically inert extenders or carriers such as are typically employed for facilitating dispersion of active ingredients for agricultural chemical applications. These formulations typically contain about from 0.5 to 95 wt% of the present compound, and optionally can contain compatible miticides, insecticides, fungicides, etc., and the remainder biologically inert material including dispersing agents, emulsifying agents, wetting agents and carriers.

Such formulation can be formulated as sprays, dusts, or granules and applied to mite eggs and/or their environment or hosts susceptible to mite attack. They can be formulated as granules of large particle size, as powdery dusts, as wettable powders, as emulsifiable concentrates, as solutions, or as any of several other known types of formulations, depending on the desired mode of application. (Wettable powders generally refers to a form of finely divided particles which disperse readily in water or other dispersant.) Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65-80 wt % silica and 35-20 wt % of the compound(s) of the invention.

Useful liquid concentrates include the emulsifiable concentrates, which are homogeneous liquid or paste compositions which are readily dispersed in water to other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or other liquid carrier, and then applied as a spray or paint to the area to be treated.

Optimum formulation concentrations and the manner and frequency of application may vary somewhat with the particular species of mite eggs, the degree of infestations, the environment (e.g. rainfall), and can be obtained by routine experimentation.

A further understanding of the invention can be had from the following non-limiting examples. Wherein, unless expressly stated to the contrary, all temperatures and temperature ranges refer to the centigrade (or Celsius) system and the term "room temperature" refers to about 20°-25° C.

The term "percent" or "%" refers to weight percent and the term "mol" or "mols" refers to gram mols. Where necessary, examples are repeated to provide sufficient quantities of starting materials for subsequent examples. The process of the reactions were monitored by gas phase chromatography and final purities were determined by assay.

EXAMPLE 1

This example illustrates the process of the invention for preparing (substituted phenoxy)benzenes.

In this example 2143 g (22.77 mol) of phenol and 906 g (22.66 mol) of sodium hydroxide were mixed together in a stirred mixture of 5.5 liters of dimethyl sulfoxide and 5.5 liters of toluene at room temperature. The mixture was then heated at reflux for 54 hours. The water formed by the reaction was removed along with a substantial portion of the toluene and a small amount of the dimethyl sulfoxide (total volume collected 4910 ml of which 690 ml were water). The temperature of the remaining reaction mixture, now containing sodium phenolate, was permitted to drop to 155° C. and 44 g of powdered copper was added. 4730 g (22 mol) of 1,2-dichloro-4-trifluoromethylbenzene was then added dropwise while maintaining the reaction mixture at 153°-155° C. After addition of the 1,2-dichloro-4-trifluoromethylbenzene, the reaction mixture was maintained at 155° C. for about 30 minutes and then allowed to stand overnight (about 12 hours) at room temperature. The reaction mixture was poured onto cold 0.5% HCl. phase separated and extracted with methylene chloride. Combined organics were washed with 5% sodium hydroxide and with water, dried over magnesium sulfate and silica, and filtered. The filtrate was then stripped (evaporated) affording 5906 g of 4-(2-chloro-4-trifluoromethylphenoxy)benzene as a yellow oil.

Similarly, 4-(2-trifluoromethyl-4-chlorophenoxy)-benzene is prepared by following the same procedure but using 1,4-dichloro-2-trifluoromethylbenzene in place of 1,2-dichloro-4-trifluoromethylbenzene.

EXAMPLE 2

This example illustrates the process of the invention for preparing 1-acetyl-4-(substituted phenoxy)benzenes.

In this example 1079 g (13.75 mols) of acetyl chloride was slowly added over one hour to a stirred mixture containing 2230 g (13.75 mols) of ferric chloride in 3450 ml of methylene chloride maintained at 16½ to 17° C. 3408 g (12.5 mols) of (2-chloro-4-trifluoromethylphenoxy)benzene was then slowly added dropwise to the mixture over a period of 3 hours and 13 minutes, during which addition the temperature of the mixture was maintained between 18.5° to 20° C. (The rate of addition was controlled such that the (2-chloro-4-trifluoromethylphenoxy)benzene was essentially consumed as it was added.) The reaction although essentially complete was stirred overnight at room temperature (about 20°). A sample was then examined by gas chromatography and indicated less than 2% of the (2-chloro-4-trifluoromethyl-phenoxy)benzene starting material remained in the reaction mixture.

The reaction mixture was then cooled to 15° C. and 6250 ml of water was slowly added over 1½ hours while maintaining the temperature of the reaction mixture at 17°-19° C. The resulting mixture was then stirred for 1 hour at room temperature and then 6250 ml of hexane was added. The mixture was phase-separated and extracted with hexane. The combined organics were washed with water and with 5% sodium bicarbonate, dried over magnesium sulfate and silica, filtered and stripped. The resulting oil/solid was recrystallized from isopropyl alcohol-hexane, yielding 2073 g of 1-acetyl-4-(2-chloro-4-trifluoromethylphenoxy)benzene.

The mother liquor was purified through formation of the semi-carbazone by adding the stripped mother liquor (913 g) to a solution of equimolar amounts of semicarbazide hydrochloride (about 2.92 mol) and sodium acetate in water-ethanol. The mixture was heated at 32°-76° for 3-4 hours. The resultant white solid was freed of impurities by rinsing with ethanol and hexane.

This solid was refluxed for 1 hour in a mixture of 350 ml concentrated hydrochloric acid, 1 liter water, and 500 ml ethanol. The mixture was cooled, phase-separated and extracted with hexane. The combined organics were washed with water and with 5% aqueous NaOH, dried over magnesium sulfate, filtered, stripped and recrystallized from isopropyl alcohol-hexane yielding 330 g of 1-acetyl-4-(2-chloro-4-trifluoromethylphenoxy)benzene.

Similarly, 1-acetyl-2-(trifluoromethyl-4-chlorophenoxy)benzene is prepared by following the same procedure but using (2-trifluoromethyl-4-chlorophenoxy)benzene in place of (2-chloro-4-trifluoromethylphenoxy)benzene.

EXAMPLE 3

This example illustrates the final step in the present process for preparing 1-dichloroacyl-4-(substituted phenoxy)benzene products.

In this example 4532 g (14.4 m) of 1-acetyl-4-(2-chloro-4-trifluoromethylphenoxy)benzene was admixed with 4550 ml of glacial acetic acid. The temperature of the mixture was raised to 38° C. and chlorine was then bubbled into the mixture for 2½ hours. During this period the temperature of the mixture rose to a high of 45° C. The addition of chlorine was then discontinued overnight (reaction mixture allowed to stand at room temperature) and was continued the following morning for another 7½ hours. Upon resumption of the addition of chlorine the reaction mixture was at 15° C. and rose to a high of 56° C. during the addition of chlorine. The majority of the chlorine was added while maintaining a reaction mixture temperature at 45°–55° C. It was noted that when a total 2231 g of chlorine had been taken up the exotherm stopped. Another 18 g of chlorine was bubbled into the reaction mixture (total chlorine added was 2349 g) and the mixture allowed to stand at room temperature for 48 hours.

The reaction mixture was poured onto ice-water, and extracted with methylene chloride. The combined organics were washed with water and with sodium bicarbonate solution, dried over magnesium sulfate and silica, filtered and stripped to an orange oil. Crystallization from isopropyl alcohol-hexane yielded 4371 g. 1-dichloroacetyl-4-(2-chloro-4-trifluoromethylphenoxy)benzene [white solid:m.p. 40°–41° C.].

Thus, it can be seen that the above processes of the invention afford a very pure product without resorting to sophisticated purification procedures.

Similarly, 1-dichloroacetyl-4-(2-trifluoromethyl-4-chlorophenoxy)benzene is prepared by using 1-acetyl-4-(2-trifluoromethyl-4-chlorophenoxy)benzene.

Obviously many modifications and variations of the invention, described hereinabove and below in the claims, can be made without departing from the essence and scope thereof.

What is claimed is:

1. A process for preparing a compound having the formula

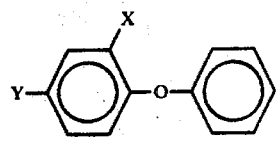 (C)

wherein one of X or Y is chloro and the other is trifluoromethyl, which comprises contacting the corresponding compound having the formula

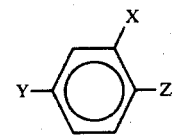 (B)

wherein X and Y are as defined hereinabove and Z is chloro with an alkali metal phenolate in the presence of a catalytically effective amount of a copper catalyst in dimethylsulfoxide at temperatures in the range of about from 145° to 165° C., under substantially anhydrous reactive conditions thereby yielding the compound of formula C.

2. The process of claim 1 wherein said copper catalyst is powdered copper.

3. The process of claim 2 wherein said process is conducted at temperatures in the range of about from 150°–160° C.

4. The process of claim 1 wherein the compound of formula B is 1,2-dichloro-4-trifluoromethylbenzene and the compound of formula C is 4-(2-chloro-4-trifluoromethylphenoxy)benzene.

5. The process of claim 1 wherein the compound of formula B is 1,4-dichloro-2-trifluoromethylbenzene and the compound of formula C is 4-(2-trifluoromethyl-4-chlorophenoxy)benzene.

6. The process of claim 1 wherein about from 2 to 6 mols of said reactant of formula B is used per liter of dimethylsulfoxide.

7. A process for preparing a compound having the formula

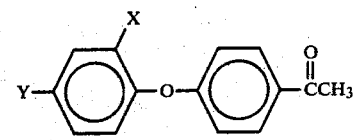 (E)

wherein one of X or Y is chloro and the other is trifluoromethyl, which comprises contacting the corresponding compound of the formula

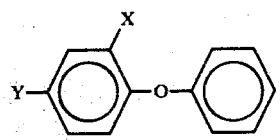 (C)

wherein X and Y are as defined hereinabove, with acetyl chloride in the presence of about from 1 to 1.3 mols of ferric chloride per mole of acetyl chloride in the solvent methylene chloride at temperatures in the range of about from 0° to 30° C., under substantially anhydrous reaction conditions thereby yielding the corresponding compound of formula E, and wherein said acetyl chloride and said compound of formula C are contacted by adding said compound of formula C to a mixture comprising said acetyl chloride said ferric chloride and said solvent, at a controlled rate such that said compound of formula C is substantially consumed upon said contact thereby substantially preventing its accumulation in said mixture.

8. The process of claim 6 wherein the amount of said ferric chloride is about from 1 to 1.15 mols of said ferric chloride per mol of said acetyl chloride.

9. The process of claim 7 wherein about from 1 to 1.5 mols of said acetyl chloride are used per mol of the compound of formula C.

10. The process of claim 7 wherein said process is conducted at temperatures in the range of about from 15° to 25° C.

11. The process of claim 7 wherein about from 1 to 1.2 mols of acetyl chloride are used per mol of compound of formula C.

12. The process of claim 7 wherein about from 1 to 10 mols of compound of formula C are used per liter of said methylene chloride.

13. A process for preparing a compound having the formula

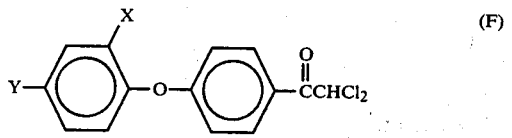

wherein one of X or Y is chloro and the other is trifluoromethyl,
which comprises the steps of
(a) contacting the corresponding compound of the formula

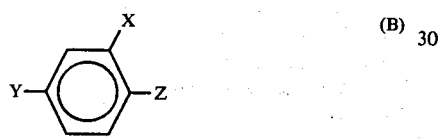

wherein X and Y are as defined hereinabove and Z is chloro with an alkali metal phenolate in the presence of a catalytically effective amount of powdered copper in dimethylsulfoxide at temperatures in the range of about from 150°-160° C. under substantially anhydrous reactive conditions thereby yielding a compound having the formula

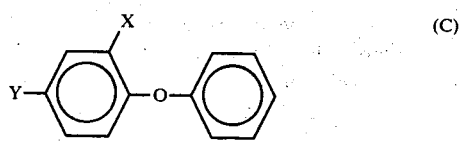

wherein X and Y are as defined hereinabove
(b) contacting the product of step (a) of formula (C) with acetyl chloride in the presence of about from 1 to 1.15 mols of ferric chloride per mol of said acetyl chloride in methylene chloride at temperatures in the range of about from 15° to 25° C. and wherein about 1 to 1.2 mols of said acetyl chloride are used per mol of the compound of formula C, under substantially anhydrous reactive conditions and wherein said compound of formula C is added at a controlled rate to a mixture comprising said acetyl chloride, said ferric chloride, and said methylene chloride, thereby yielding the corresponding compound of the formula

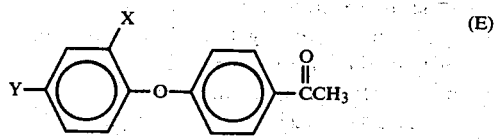

wherein X and Y are as defined hereinabove, and;
(c) contacting the product of step (b) of formula E with chlorine in an inert organic solvent at temperatures in the range of about from 40°-55° C. under reactive conditions thereby yielding the corresponding compound of formula F.

14. The process of claim 13 wherein said inert organic solvent of step (c) is glacial acetic acid.

* * * * *